United States Patent
Van Keersop et al.

(10) Patent No.: US 9,775,522 B2
(45) Date of Patent: Oct. 3, 2017

(54) INTEGRATION DELAYED OPTICAL FEEDBACK IN IMAGE GUIDANCE

(71) Applicant: KONINKLIJKE PHILIPS N.V., Eindhoven (NL)

(72) Inventors: Arnoldus Theodorus Martinus Hendrics Van Keersop, Eindhoven (NL); Rami Nachabe, Eindhoven (NL); Bernardus Hendrikus Wilhelmus Hendriks, Eindhoven (NL); Christian Reich, Eindhoven (NL); Manfred Muller, Eindhoven (NL); Jeroen Jan Lambertus Horikx, Weert (NL); Robert Johannes Frederik Homan, Batenburg (NL); Nicolaas Jan Noordhoek, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 371 days.

(21) Appl. No.: 14/386,836

(22) PCT Filed: Mar. 26, 2013

(86) PCT No.: PCT/IB2013/052400
§ 371 (c)(1),
(2) Date: Sep. 22, 2014

(87) PCT Pub. No.: WO2013/144841
PCT Pub. Date: Oct. 3, 2013

(65) Prior Publication Data
US 2015/0080712 A1    Mar. 19, 2015

Related U.S. Application Data

(60) Provisional application No. 61/615,922, filed on Mar. 27, 2012.

(51) Int. Cl.
*A61B 5/05* (2006.01)
*A61B 5/00* (2006.01)
(Continued)

(52) U.S. Cl.
CPC .......... *A61B 5/0084* (2013.01); *A61B 5/0075* (2013.01); *A61B 5/6848* (2013.01);
(Continued)

(58) Field of Classification Search
CPC ... A61B 5/0084; A61B 5/7425; A61B 5/0075; A61B 5/6848; A61B 2090/306;
(Continued)

(56) References Cited

U.S. PATENT DOCUMENTS 7,925,327 B2 * 4/2011 Weese ............... A61B 8/12
600/424
8,306,604 B2 * 11/2012 Parks ............... A61B 6/12
382/132

(Continued)

FOREIGN PATENT DOCUMENTS

WO    2011004288 A1    1/2011

OTHER PUBLICATIONS

John M. Racadio E Al, "Live 3D Guidance in the Interventional Radiology Suite", Am. J. Roentgenol, Interventional Radiology Pictorial Essay, AJR:189 (6), Dec. 2007, pp. W357-W364.
(Continued)

*Primary Examiner* — Sanjay Cattungal

(57) ABSTRACT

The present invention relates to a system (10) for navigating and positioning an instrument (12, 40, 112) in a body (14). The instrument (12, 40, 112) is detectable by the system (10) and the system (10) displays a view to an operator. The instrument (12, 40, 112) is adapted to identify tissue parameters. The system (10) is adapted to display an image being a combined image of the interior of a body (14) and an
(Continued)

indication of the tissue parameter at the appropriate earlier locations. The present invention further relates to a method (44) including determining tissue parameters and displaying the parameters in an image of a body (14). The present invention further relates to a software implemented method (44) for being executed on a digital processor. The present invention further relates to an instrument (12, 40, 112).

15 Claims, 3 Drawing Sheets

(51) Int. Cl.
    *A61B 5/06*           (2006.01)
    *A61B 17/00*         (2006.01)
    *A61B 6/12*          (2006.01)
    *A61B 90/00*         (2016.01)
    *A61B 90/30*         (2016.01)
    *A61B 34/20*         (2016.01)

(52) U.S. Cl.
    CPC .......... *A61B 5/7425* (2013.01); *A61B 5/0071* (2013.01); *A61B 5/061* (2013.01); *A61B 6/12* (2013.01); *A61B 2017/00061* (2013.01); *A61B 2034/2051* (2016.02); *A61B 2090/306* (2016.02); *A61B 2090/364* (2016.02); *A61B 2090/376* (2016.02)

(58) Field of Classification Search
    CPC ...... A61B 2034/2051; A61B 2090/364; A61B 2090/376; A61B 6/12; A61B 2017/00061; A61B 5/0071; A61B 5/061
    USPC .................................. 600/407–430; 606/130
    See application file for complete search history.

(56) References Cited

U.S. PATENT DOCUMENTS

| | | |
|---|---|---|
| 9,030,552 B2 | 5/2015 | Simon |
| 2006/0247517 A1* | 11/2006 | Labadie .................. A61B 5/06 600/426 |
| 2007/0012555 A1 | 1/2007 | Fuchigami et al. |
| 2007/0049817 A1 | 3/2007 | Preiss et al. |
| 2007/0135803 A1 | 6/2007 | Belson |
| 2007/0197905 A1 | 8/2007 | Timinger et al. |
| 2009/0257554 A1* | 10/2009 | Parks ...................... A61B 6/12 378/44 |
| 2010/0274120 A1 | 10/2010 | Heuscher |
| 2010/0286507 A1 | 11/2010 | Paassilta et al. |
| 2010/0312096 A1 | 12/2010 | Guttman et al. |
| 2011/0236868 A1 | 9/2011 | Bronstein et al. |
| 2012/0226150 A1 | 9/2012 | Balicki et al. |
| 2015/0080712 A1 | 3/2015 | Van Keersop et al. |
| 2016/0073909 A1 | 3/2016 | Zand et al. |

OTHER PUBLICATIONS

Rami Nachabe et al, "Effect of bile absorption coefficients on the estimation of liver tissue optical properties and related implications in discriminating healthy and tumorous samples", Biomedical Optics Express 614, Mar. 1, 2011, vol. 2. No. 3.

R. Nachabe et al., "Estimation of biological chromophores using diffuse optical spectroscopy: benefit of extending the UV-VIS wavelength range to include 1000 to 1600 nm", Biomedical Optics Express, 2010, p. 1.

* cited by examiner

INTEGRATION DELAYED OPTICAL FEEDBACK IN IMAGE GUIDANCE

CROSS-REFERENCE TO PRIOR APPLICATIONS

This application is the U.S. National Phase application under 35 U.S.C. §371 of International Application Serial No. PCT/IB2013/052400, filed on Mar. 26, 2013, which claims the benefit of U.S. Application Ser. No. 61/615,922, filed on Mar. 27, 2012. These applications are hereby incorporated by reference herein.

FIELD OF THE INVENTION

The present invention relates to a system for integrating optical feedback with imaging and guidance of instruments. The present invention relates to a method for preparing an image to be displayed on a display unit. The present invention relates to a software implemented method for being executed on a digital processor. The present invention relates to an instrument for use with a guidance system.

BACKGROUND OF THE INVENTION

When positioning an instrument in a patient there is a need for being providing real-time position information relating to the instrument. Further as imaging methods for tissue most often provides images where it is not easy to identify tissue type.

The inventor of the present invention has appreciated that an improved system and method is of benefit, and has in consequence devised the present invention.

Needles are one of many devices or instruments which are placed in specific locations within a body based on pre-procedural images. The images are obtained with various modalities (imaging technologies) such as magnetic resonance imaging, computed tomography or image reconstruction such as XperCT™. One goal of placement is to minimize damage to surrounding tissues by carefully selecting the path of the needle during placement.

With X-ray instrument guidance it is possible to allow for almost real-time monitoring of instrument guidance under for instance fluoroscopy. An optical needle is one example of a device configured to provide tissue feedback as guidance and information. The optical needle transmits an optical signal to the tissue and receives. By combining these two techniques both the instrument tip location with respect to the body as well as the display of tissue information at that location is possible.

To obtain tissue information using an optical signal optical spectra has to be acquired and processed to create the tissue information. Furthermore this information must be sent to the imaging device, linked to the instrument position in the image, and finally displayed. All these steps require an amount of time and may cause that the displayed data is no longer up to date with the actual location. Especially when the instrument is advanced relatively fast, the tissue information may be lagging behind.

SUMMARY OF THE INVENTION

It would be advantageous to achieve a system where an image is displayed wherein both position of an instrument as well as tissue type is displayed. In general, the invention preferably seeks to mitigate, alleviate or eliminate one or more of the above mentioned disadvantages singly or in any combination. In particular, it may be seen as an object of the present invention to provide a method that solves the above mentioned problems, or other problems, of the prior art.

To better address one or more of these concerns, in a first aspect of the invention a system for navigating and positioning an instrument in a body is presented. In the system the instrument comprises a sensor for optical inspection of tissue, the instrument is configured to generate a tissue signal. The system comprises a tissue-type determination device configured to receiving the tissue signal from the instrument at times Ts, the tissue-type determination device configured to determine a set of parameters indicative of tissue type based on the tissue signal from the instrument. The system comprises a medical imaging device configured for forming an image of the interior of the body, the medical imaging device recording a temporal sequence of images with each a timestamp Tf. The system comprises an image processing unit configured to establish a combined image of the interior of the body at timestamp Tf and an indication of tissue-type at the spatial position of the instrument for a timestamp Ts so that the combined image of the interior of the body comprises the current instrument position and the indication of tissue-type at the position of the instrument at time Ts. The system comprises a display unit for displaying the combined image of the interior of the body. The interval between Tf time stamps is relatively lower than the interval between Ts time stamps. The image of the interior of the body is the most current image, and the time at which the tissue signal was recorded will be at an earlier point in time due to the calculation process. Further, the indication of tissue-type is displayed at the location corresponding to the position of the instrument at that point in time when the signal was recorded. Thereby the indication of tissue-type may be seen as lagging behind the instrument in the combined image.

By having a device providing an image of the interior of a body where an instrument is present, it is possible for a person using the instrument to guide the instrument to a desired location inside the body without having to open the body to a large extend. For guidance purposes it is important to have the most up-to-date image as possible.

In the images obtained this way, e.g. x-ray images or ultrasound images, it may be difficult, or even impossible, to accurately determine which type of tissue is present at the instrument, e.g. at tissue boundaries. The tissue determination device provides this information. By combining such two pieces of information into a single image, it is possible for a person operating the instrument with high accuracy to determine if the instrument is in the intended position. Obtaining tissue information requires an amount of time and may cause that the displayed data is no longer up-to-date with the actual location of the instrument tip. Especially when the instrument is advanced relatively fast, the tissue information may be lagging behind.

As there may be time consuming calculations needed for determining tissue type parameters the system will provide an image, e.g. seen as live video or real-time video, where tissue information appears when it is available. By combining the two techniques in this system both current instrument location with respect to the body as well as the tissue information at an earlier location can be displayed.

The instrument may in the present context be an interventional device. The instrument or interventional device may comprise a first guide for guiding photons from the light source to an exit position on a distal end of the interventional device, the photons being emittable from the exit position, and a second guide for guiding photons from an entry position on the distal end of the interventional device and to the optical detector.

It is understood that in one particular embodiment, the first guide and the second guide may be one guide, such as the first guide is identical to the second guide. In another particular embodiment, the first guide and the second guide are two separate guides.

An interventional device is generally known in the art, and may include any one of an endoscope, a catheter, a biopsy needle. Integrating optical fibers in the interventional device allows inspection of the optical characteristics of the tissue sample and may allow discrimination of pathology tissue from normal tissue. In a particular embodiment, there is provided an interventional device being suited both for Diffuse Reflectance Spectroscopy (DRS) and/or fluorescence spectroscopy. It is noted that the constraint that the interventional device should be applicable for fluorescence spectroscopy puts some additional constraints on the interventional device. For instance the fibers used for fluorescence spectroscopy must not produce too much autofluorescence themselves and the separation between fiber ends for the fibers respectively connected to source and detector may be shorter compared to the same distance for DRS.

In another embodiment, the exit position and the entry position are spatially separated and spatially oriented so that the entry position is not intersected by ballistic photons emitted from the exit position, when the distal end of the interventional device is placed adjacent the associated sample. It is understood that the entry position is not intersected by ballistic photons emitted from the exit position, at least from a practical point of view. For all practical purposes, the number of ballistic photons hitting the entry position is non-zero but negligible.

The sensor for optical inspection of tissue may be configured for determining water content, fat content and/or blood. These types of tissue information may help the person operating the instrument to determine where the instrument is, and possibly in which organ the instrument, or the tip of the instrument, is located. The sensor in the instrument may advantageously be located at the tip of the instrument. The instrument may be in the form of a needle. The instrument may have an elongated geometry and have a circular cross-section.

During any procedure accurate knowledge about the location of the needle tip is important, but proper guidance relative to the image may not be available. For instance, in the case of a CT guided biopsy, the number of images acquired is limited due to concerns about radiation exposure to the patient. If, due to the lack of precise information, incorrect tissues are targeted, there is a risk of an inaccurate diagnosis or a need for repeated procedures, which involves additional risk to the patient and increased costs.

One method of tracking the position of the needle tip relative to pre-procedural image is to place a marker(s) on the portion of the needle external to the patient and to track the marker in real time by means of a variety of sensors; given an estimation of the needle geometry the computed needle tip position can then be mapped in real time to the pre-procedural image. For instance, optical tracking of the needle can be performed with visual markers using two or more imaging cameras. Alternatively, Electro-Magnetic (EM) navigation can be performed by means of a small EM coil marker placed on the needle and tracked by a set of sensors external to the needle.

While the location and orientation of the tip is important, the real-time information relating to the tissue in front of the instrument is also important to the person operating the instrument.

Advantageously a color saturation level may be used as indicative of a measured quantity of a tissue parameter. This provides an intuitive indication of a measured quantity.

In the system the tissue-type determination device may be connected to a spectrometer configured for transforming a signal from the tissue-type determination device into a spectrum. Using optical signals is a secure, non-invasive method for determining tissue parameters. Therefore it could be advantageous to determine the tissue parameter based on the spectrum.

Instead of displaying dots, the tissue parameter may be displayed as a solid line and the width of the line is an indicator of the inaccuracy. This would provide an image where the tissue parameter may be displayed as a curve indicating the path of the instrument.

With X-ray instrument guidance it is possible to allow for almost real-time monitoring of the instrument guidance under for instance fluoroscopy. The spectroscopic technology of the PhotonicNeedle is one example of how to provide tissue feedback. By combining the two techniques, both the instrument tip location with respect to the body as well as the tissue information at that location can be displayed. Obtaining PhotonicNeedle tissue information requires an amount of time and may cause that the displayed data is no longer up-to-date with the actual location of the instrument tip. Especially when the instrument is advanced relatively fast, the tissue information may be lagging behind.

The present invention proposes to use video processing to find the "old" or previous location of the instrument tip that belongs to the delayed tissue information. This information is then displayed at this "old" location instead of at the current location of the instrument tip. Video frames of (X Y pixels) are captured at timestamps Tf. For each video frame, the computer algorithm determines the position (x,y) of the instrument tip in the frame (X Y). Tf together with (x,y) are stored in a instrument-position list. The current video frame is displayed on the display unit, showing the body with the current instrument position (Xc,Yc).

The tissue-type determination device may be an optical console and the guidance system may be arranged so as to obtain diffuse reflectance spectrum and/or a fluorescence spectroscopy spectrum and/or Raman spectrum from the optical console. Light is to be broadly construed as electromagnetic radiation comprising wavelength intervals including visible, ultraviolet (UV), near infrared (NIR), infrared (IR), X-ray. The term optical is to be understood as relating to light.

An optical spectrum is understood to be information related to a plurality of wavelengths of light, such as an intensity parameter, an absorption parameter, a scattering parameter or a transmission parameter given for a plurality of wavelengths of light. A continuous spectrum represents spectral information, but it is further understood, that information related to light at discrete wavelengths may represents an optical spectrum.

A spectrometer is understood as is common in the art. It is understood, that the spectrometer comprises means for selecting wavelengths, such as transmission filters or gratings. Alternatively, wavelength specific light sources, such as light emitting diodes or LASERs, may be used or wavelength specific optical detectors may be used. A spectral filtration may occur at different places in the system, for instance it may occur between the second light source and an interventional device, it may occur in the interventional device, or it may occur between the interventional device and the optical detector.

In an embodiment the determination of the set of parameters indicative of tissue type comprises performing multivariate statistical analysis, such as PCA or partial least squares discriminant analysis. Multivariate analysis is commonly known in the art and understood to include Principal Components Analysis (PCA) and least squares discriminant analysis.

In a second aspect a method is presented, the method comprises the steps of: determining a sequence of images of the interior of a body at times Tf, determining a sequence of sensor positions in the images of the interior of the body at times Tf, determining at time Ts an indication of tissue-type at the spatial position of the sensor for a timestamp Ts, determining for time Ts an estimated sensor position based on a part of the temporal sequence of sensor positions for a time period around time Ts, and displaying on a display unit an image being a combination of an image of the interior of a body at Tf and a representation of tissue parameter at the sensor position at time Ts. Hereby the method combines information about the position of an instrument in a body with tissue parameters, which enable a person using the instrument to gain information on both instrument position and information regarding which tissue is present at the instrument. The method includes displaying at least the most current information regarding both.

Advantageously a color saturation level may be determined representative of quantity of determined tissue parameter. The color saturation level is an intuitive representation of quantity and is easily viewable on a screen.

The tissue parameter may be determined using an optical sensor and the method comprises using a spectrum determined from a signal from the optical sensor for determining the tissue parameter. As mentioned above the use of an optical signal is a safe, non-intrusive method of determining tissue parameters.

Alternatively to the display of dots, the tissue parameter is displayed as a solid line and the width of the line may be an indicator of the inaccuracy. When displaying the parameters as a line, a continuous representation of the parameter may be shown to the user. This will allow the user to follow, or 'back-track', the instrument path through the body.

The method according to the second aspect may be implemented in software and used in controlling a system according to the first aspect. This could be expressed as a software implemented method for being executed on a digital processor, the software implemented method comprising determining a sequence of images of the interior of a body at times Tf, determining a sequence of sensor positions in the images of the interior of the body at times Tf (30, 32, 34), determining at time Ts a tissue parameter at sensor position of the instrument, determining for time Ts an estimated sensor position based on a part of the temporal sequence of sensor positions for a time period around time Ts, and displaying on a display unit an image being a combination of an image of the interior of a body at Tf and a representation of tissue parameter at the sensor position at time Ts. The software implemented method may include any feature mentioned in relation to the second aspect. The software implemented method may be executed on a processor in a system according to the first aspect.

A fourth aspect of the present invention relates to an instrument for use in a system for guiding the instrument in a body, the instrument comprising an optical probe, the system for guiding the instrument comprising: a tissue-type determination device configured to receiving the tissue signal from the instrument at times Ts, the tissue-type determination device configured to determine a set of parameters indicative of tissue type based on the tissue signal from the instrument, a medical imaging device configured for forming an image of the interior of the body, the medical imaging device recording a temporal sequence of images with each a timestamp Tf (30, 32, 34), an image processing unit combining an image of the interior of the body at timestamp Tf (30, 32, 34) and an indication of tissue-type at the spatial position of the sensor for a timestamp Ts, and a display unit for displaying the combined image of the body. The instrument according to the fourth aspect may advantageously be used with a system according to the first aspect. The instrument according to the fourth aspect may include any features mentioned in relation to any of the other aspects.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
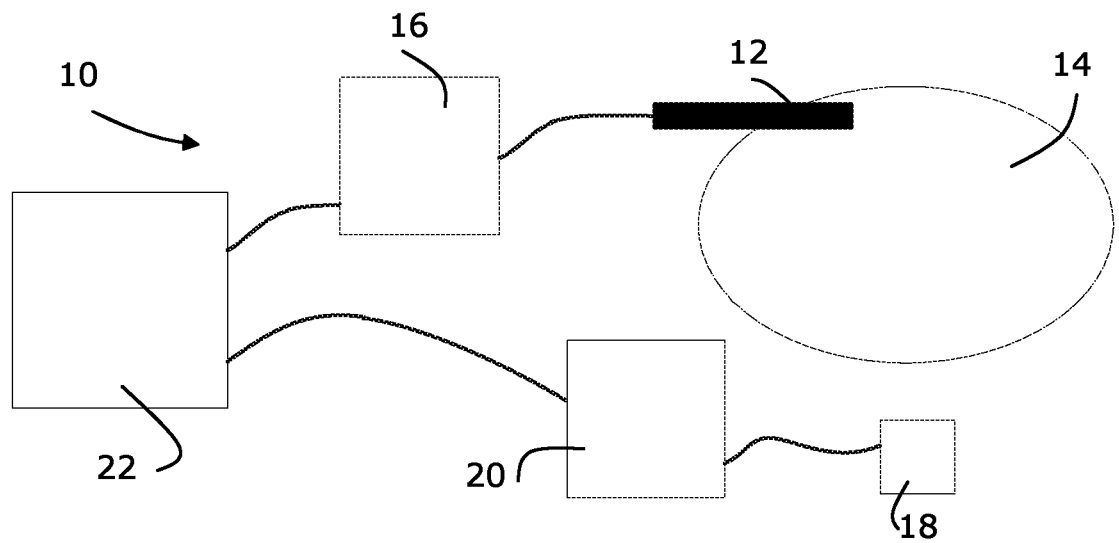
FIG. 1 is a schematic illustration of elements of a system according to the present invention.

An embodiment of the invention is illustrated in FIG. 1 where a system 10 for navigating and positioning an instrument 12 in a body 14 is illustrated. The instrument 12 comprises a sensor, not illustrated here, for optical inspection of tissue in the body 14. The instrument 12 is configured to generate a tissue signal. The system 10 comprises a tissue-type determination device 16 configured to receive the tissue signal from the instrument 12. The tissue signals are received at times Ts. The tissue-type determination device 16 is configured to determine a set of parameters indicative of tissue type based on the tissue signal from the instrument 12. This information is stored in a storage device. The system 10 comprises a medical imaging device 18 configured for forming an image of the interior of the body 14. The medical imaging device 18 records a temporal sequence of images each with a timestamp Tf. The system 10 comprises an image processing unit (20) configured to establish a combined image of the interior of the body (14) at timestamp Tf (30, 32, 34) and an indication of tissue-type at the spatial position of the instrument for a timestamp Ts (24, 26, 28) so that the combined image of the interior of the body comprises the current instrument position and the indication of tissue-type at the position of the instrument at time Ts, thereby the person operating the instrument 12 is able to gain information on instrument 12 position as well as indication of tissue type in the vicinity of the instrument 12. The system 10 comprises a display unit 22 for displaying the combined image of the body. The display could be a color monitor or other type of screen.

The imaging device could for instance be an X-ray device capable of recording or generating images of the interior of the body 14. The system records the data from the different sensors and detectors. This data is then used for two purposes, the real-time display to the user and for later analysis. For the real-time display there is a need for displaying the processed data as quick as possible. When the instrument 12 is not being moved fast, there is more time for processing the data and consequently a higher accuracy may be achieved. This is possible as the person using the instrument 12 is moving the instrument slowly or holding the instrument as still as possible.

The instrument 12 may be hand-held or supported by a guiding system or part of or attached to a robot arm or the like.

The system 10 according to the present invention is an integral solution for providing the most important tissue specific parameters being visualized at the instrument position tip in the X-ray film with colored dots. For instance blood, fat and water with, respectively, red green and blue dots. The saturation value of each color is a measure for the measured quantity. In one embodiment old information (old dots) at previous instrument tip locations is not erased but kept in the X-ray video. With this method of representation we establish that (a) the most current information is available at the field of attention (instrument tip) and (b) the information of the previously passed tissue remains available. Alternatively old information (old dots) at previous instrument tip locations is faded over a longer period of time.

Due to the time delay however, the tissue type information arriving at the X-ray guidance system is not representative for the tissue at the instrument tip when the instrument is moved. This problem can be solved by applying a position correction of the location when the tissue parameter(s) is shown at the screen: During X-ray instrument guidance, for instance during fluoroscopy, video frames are stored. With video processing it is possible to determine the location of the instrument tip within each video frame. Consequently the instrument tip location as a function of time may be known. When both processing devices are time-synchronized, the instrument tip location belonging to the delayed information can be retrieved and the tissue parameter information can be displayed as colored dots at the retrieved location instead of the instrument tip location.

To perform an optical analysis of the tissue in front of the instrument 12 three steps have to be performed. In the first step spectroscopic measurement is performed. Light is send to the distal end of the probe where it interacts with the tissue and the light reaching the light guide of the probe again is guided to a spectrometer. The spectrometer transforms the signal into a spectrum. Each measured spectrum has a timestamp Ts at which the measurement did start. In the second step the measured spectra is translated into tissue parameters for instance in the way described in R. Nachabé et al., "Estimation of biological chromophores using diffuse optical spectroscopy: benefit of extending the UV-VIS wavelength range to include 1000 to 1600 nm", Biomedical Optics Express 1, 2010. In the third step the optical information with the time stamp Ts is send to the image processing device 20.

Figure 3:
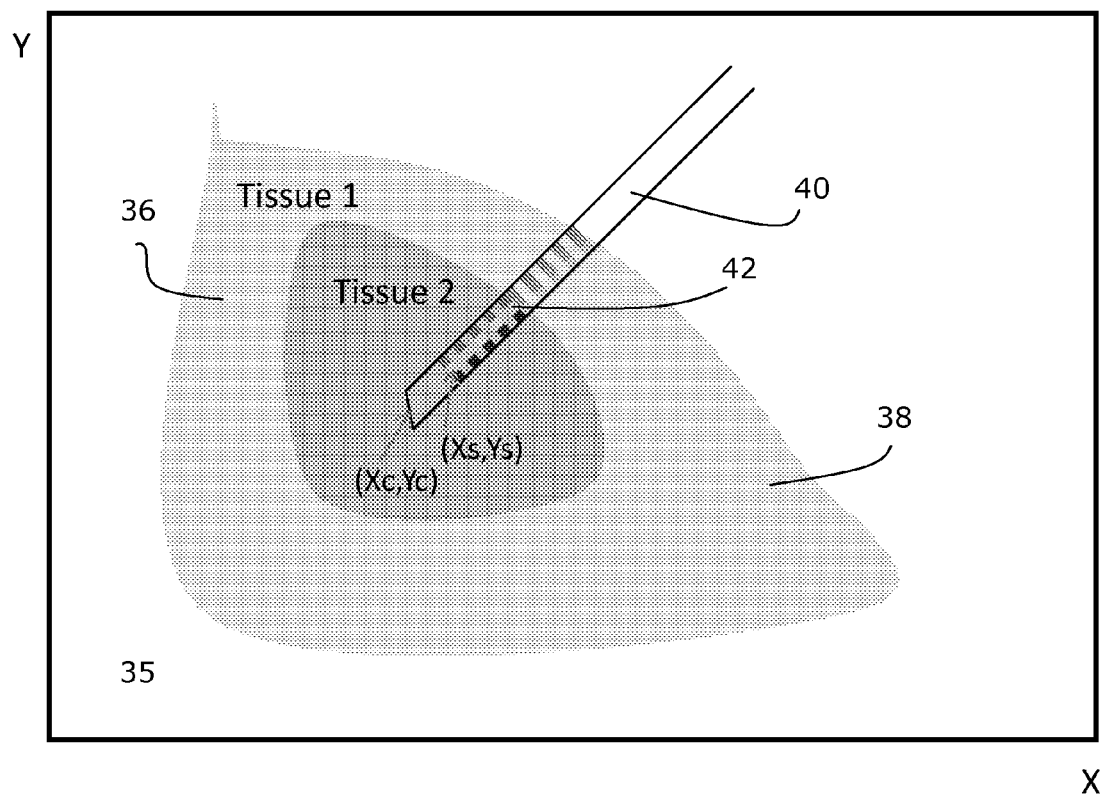
FIG. 3 is a schematic illustration of a view generated on the basis of information using the system according to the present invention.

The image processing device 20 and the tissue-type determination device 16 are time-synchronized. Continuously video frames of (X Y pixels) are captured at timestamps Tf. For each video frame, a computer algorithm determines the position (x,y) of the instrument tip in the frame (X Y). Information relating to Tf together with position of the tip (x,y) are kept in an instrument-position list stored on a storage medium, e.g. hard drive or the like. The current video frame is displayed at the displaying unit, showing the body 14 with the current instrument position (xc,yc). Such a view is illustrated in FIG. 3.

In the following two different ways of determining tissue parameters is discussed. The methods may be used separately or in combination. Other method for optical investigation of the tissue may also be used in connection with the present invention.

Figure 5:
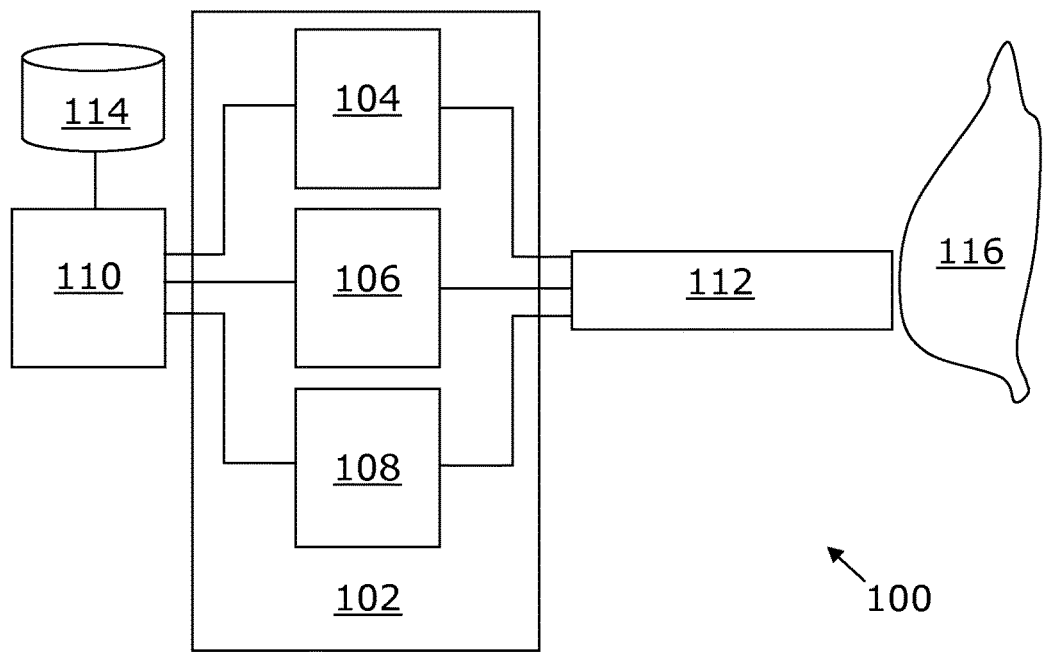
FIG. 5 shows a schematic view of an embodiment of an apparatus according to the invention.

FIG. 5 shows a schematic view of an apparatus comprising a spectrometer 102 comprising a light source 104, an optical detector 106 and an interventional device 112, where the interventional device 112 has one or more guides, such as optical elements, such as optical waveguides, capable of guiding light from the light source 104 to a distal end of the interventional device so as to emit the light at the distal end of the interventional device, and furthermore capable of guiding light back from the distal end of the interventional device to the optical detector 106. The light guides enable light to enter an associated tissue sample 116 and the light guides further enable light exiting the associated tissue sample to be collected and led to the optical detector. The apparatus thus enables procurement of measured data representative of an optical spectrum of the associated tissue sample 116. The optical detector 106 may be controlled by processor 110 so as to acquire the measured data. The processor may have access to a database 114. In a specific embodiment, the apparatus is further arranged to access the database 114, where the database comprises predetermined data representative of an optical spectrum, such as an optical spectrum of a bio molecule, such as collagen and/or elastin, such as a plurality of optical spectra of different chromophores. This may enable the processor to better determine any one of the first parameter, the distortion parameter and the second parameter.

In the specific embodiment shown there is also a second light source 108. In this embodiment the first light source 104 is a lamp suited for Diffuse Reflectance Spectroscopy (DRS) and the second light source 108 is a LASER suited for fluorescence spectroscopy. In an alternative embodiment, there may be only a single light source, such as a single lamp which may then be used in combination with a switchable filter serving to limit the range of frequencies emitted and thereby narrowing the bandwidth and thereby obtaining an appropriate bandwidth for doing fluorescence spectroscopy.

Figure 6:
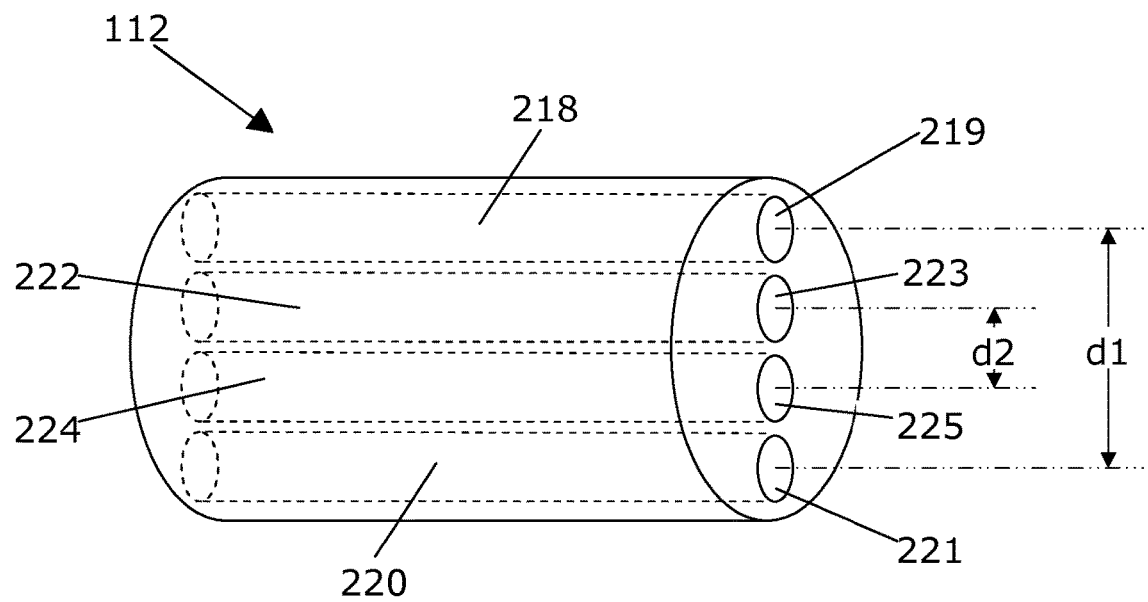
FIG. 6 shows a perspective illustration of an embodiment of an interventional device used in the system according to the invention.

FIG. 6 shows a perspective illustration of an embodiment of an interventional device 112, which interventional device comprises a first guide 219, a second guide 221, a third guide 223 and a fourth guide 225. The figure shows an exit position 219 on distal end of the first guide and an entry position 221 on a distal end of the second guide. Similarly, there is shown an exit position 223 on distal end of the third guide and an entry position 225 on a distal end of the fourth guide. The drawing is not to scale. The first, second, third and fourth guide are understood to be light guides, such as optical fibers, such as optical waveguides. Furthermore is indicated the distance d1 between an exit position 219 on the first guide 218 and an entry position 221 on the second guide 220. Still further is shown a distance d2 between an exit position 223 on the third guide 222 and an entry position 225 on the fourth guide 224. Note that in a particular embodiment the interventional device may be constructed so as to optimize d1 for Diffuse Reflectance Spectroscopy. In another particular embodiment the interventional device may be constructed so as to optimize 2 for fluorescence spectroscopy.

In a specific embodiment there is provide an optical probe, such as the interventional device 112, is a needle with optical fibers 218, 220, 222, 224 that can be connected to an optical console, such as the spectrometer 102. The optical console contains a light source 104 enabling light to be provided via one of the fibers to the distal end of the optical probe. The scattered light is collected by another fiber and is guided towards the detector 106. The optical console may also contain a LASER source 108 with a wavelength lower than 450 nm in order to induce autofluorescence in the tissue sample. The obtained data, such as the first and/or second set of measured data are processed by processor 110 using a dedicated algorithm. For instance light is coupled out of the distal tip through at least one fiber, which serves as a source, and the wavelength is swept from e.g. 500-1600 nm or a broadband light source is used. The corresponding wavelength-dependent reflection is measured by at least one other fiber, which is spatially separated from the source, such as a distance d1 of at least 0.5, such as at least 1, such as at least 2 mm apart, such as at least 5 mm apart. The amount of reflected light measured at the "detection" fiber, is determined by the absorption and scattering properties of the probed structure (e.g. tissue sample). From this signal we can deduce the concentration of the chromophores such as blood, water, fat elastin, bile, beta-carotene but also oxygenation of blood and scattering parameters. The autofluorescence is measured through a fiber that is in close vicinity with the excitation fiber, such as within a distance d2 being less than 5 mm, such as less than 2 mm, such as less than 1 mm, such as less than 0.5 mm, such as less than 0.25 mm. The measured autofluorescence is corrected for scattering and absorption such that the estimated intrinsic fluorescence is obtained. From this the concentration of fluorophores such as NADH, FAD collagen and elastin can be measured.

In a specific embodiment, the apparatus comprises a light source 104 in the form of a halogen broadband light source with an embedded shutter, an interventional device 112 with four guides and an optical detector 106 that can resolve light across a span of wavelengths, such as substantially in the visible and infrared regions of the wavelength spectrum, such as from 400 nm to 1700 nm. The apparatus may furthermore comprise a filter that rejects light for wavelengths below 465 nm which filter may be mounted in front of the optical detector 106 to reject second order light at the optical detectors during diffuse reflectance spectroscopy. The interventional device 112 has a first guide connected to the light source, the second guide connected to the optical detector 106. The centre-to-centre distance separation d1 between the exit position 219 on the first (emitting) guide 218 and the exit position 221 on the second (collecting) guide 220 may be in the millimeter range, such as at least 1 mm, such as at least 2 mm, such as 2.48 mm. All guides may be low-OH fibers of core diameters in the micron range, such as core diameter of 200 microns. Fibers containing low-OH, sometimes also called VIS-NIR fibers, are typically suitable for the visible (VIS) and near infrared (NIR) part of the optical spectrum.

In an alternative embodiment a plurality of optical detectors are applied, such as two optical detectors that can resolve light in different length regions, such as substantially in the visible and infrared regions of the wavelength spectrum respectively, such as from 400 nm to 1100 nm and from 800 nm to 1700 nm respectively.

In a particular embodiment diffuse reflectance spectroscopy is used for obtaining the first set of measured data representative of an optical spectrum and fluorescence spectroscopy is used for obtaining the second set of measured data representative of an optical spectrum. Other optical methods can be envisioned, such as fluorescence spectroscopy measurements, diffuse optical tomography by employing a plurality of optical fibers, differential path length spectroscopy, or Raman spectroscopy.

Preferably, the optical console allows for the fluorescence excitation wavelength to be changed. This could be accomplished with multiple sources that are switched or multiplexed (e.g. frequency modulated) or with a tunable source. Measuring different fluorescence emission spectra at different excitation wavelengths would provide information that is potentially relevant for differentiating collagen and elastin (and additionally different types of collagen).

Two-photon fluorescence excitation could also be utilized. This may have the benefits of deeper penetration depth relative to one-photon excitation. The volumes probed with two-photon fluorescence measurements may be more similar to the volumes probed for diffuse reflectance measurements in the infrared.

Figure 2:
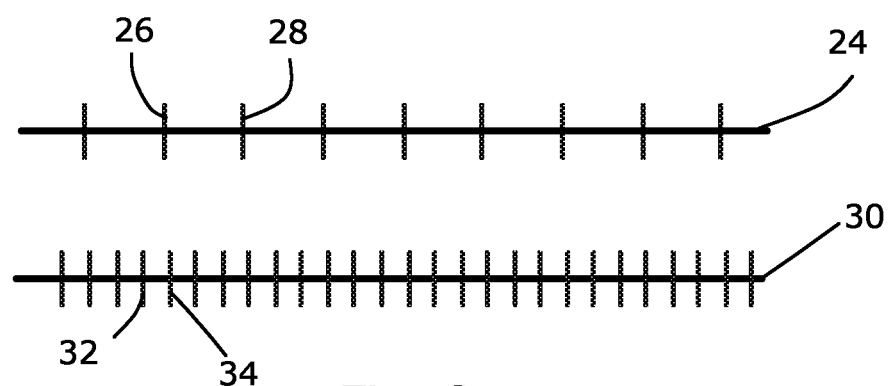
FIG. 2 is a schematic illustration of timelines when recording information.

In FIG. 2 is a schematic illustration of time sequence, where the line 24 illustrates that tissue parameters are determined at times 26 and 28, e.g. being two neighboring Ts timestamps. The temporal distance between these two timestamps 26, 28 illustrates the processing time needed to determine tissue parameters via the signal from the instrument 12.

The line 30 illustrates times 32 and 34, e.g. being two neighboring Tf timestamps, where an image is recorded by the medical imaging device 18. The temporal distance between these two timestamps 32, 24 illustrates the processing time needed to process the image in the image processing device 20.

As the time period needed for processing the tissue parameter is longer than the time period needed for processing the image of the interior of the body it is not possible to simply combine this information (or these two pieces of information) into one single image, or image sequence as a video. There is a need for displaying the most current image of the interior of the body showing the current position of the instrument so that the person using the instrument does not damage tissue or ruptures tissue unintentionally. Therefore it is not possible to simply wait until tissue type information is available.

When the optical information arrives at the tissue determination device, the belonging instrument tip position (xs, ys) can be retrieved from the instrument-position list by, for instance, interpolating Ts and then interpolating (xs,ys). The tissue parameter information is then displayed in the current video frame at position (xs,ys). In the embodiment illustrated in FIG. 3 this is done by means of colored dots. The tissue parameters could include for instance, blood, fat and water being displayed with respectively red green and blue dots.

The saturation value of each color is a measure for the measured quantity, see FIG. 3. Notice when the processing time of the data decreases, the dot-line becomes more solid and (xs,ys) will shift more towards (xc,yc).

In another embodiment the three colors can be fused into one dot with one color. The size of the dot is then a precision indicator: Large dots are measurements for high accuracy while small dots may contain large errors, i.e. low accuracy. It is also possible to determine the velocity of the instrument from the instrument-position list. The velocity of the instrument also determines the accuracy of the measurement: If the instrument is moved fast, accuracy is lost since a larger volume is sampled. Furthermore it is possible to display a solid line instead of dot and let the width of the line be an indicator of the inaccuracy.

FIG. 3 schematically illustrates a view 35 where an instrument 40 is shown. The instrument 40 penetrates a first tissue type 36 and a second tissue type 38. The dots 42 illustrate tissue parameters. Here three colors are illustrated as indicative of tissue types. In other embodiments other numbers of parameters may be used. At the position (Xs, Ys) tissue type information is displayed. Here it is seen that the instrument 40 has been advanced in a straight line as the dots are all inline. In the view 35 the tip of the instrument is indicated at (Xc,Yc).

Figure 4:
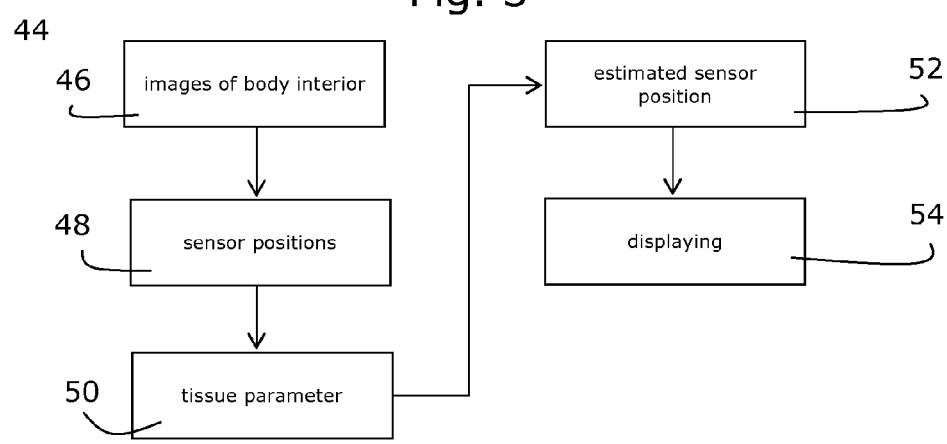
FIG. 4 is a schematic illustration of steps of a method according to the present invention.

FIG. 4 is a schematic illustration of a method 44 comprising the step of determining 46 a sequence of images of the interior of a body at times Tf. These images show among other things the current position of the instrument. The method 44 comprises the step of determining 48 a sequence of sensor positions in the images of the interior of the body at times Tf. The method 44 comprises the step of determining 50 at time Ts a tissue parameter at sensor position of the instrument. The method 44 comprises the step of determining 52 for time Ts an estimated sensor position based on a part of the temporal sequence of sensor positions for a time period around time Ts. The method 44 comprises the step of displaying 54 on a display unit an image being a combination of an image of the interior of a body at Tf and a representation of tissue parameter at the sensor position at time Ts.

The method 44 may further comprise determining a color saturation level representative of quantity of determined tissue parameter. As mentioned above this may then be displayed in the view 35.

The method 44 may comprise the step of the tissue parameter being determined using an optical sensor and the method comprises using a spectrum determined from a signal from the optical sensor for determining the tissue parameter. This allow a simple, non-invasive determination of tissue type parameters, which is of advantage to the patient as it reduces recovery period and heightens the information level for the person operating the instrument.

Alternatively to the dots illustrated in the view 35 of FIG. 3, the method may comprise the step of the tissue parameter being displayed as a solid line and the width of the line is an indicator of the inaccuracy.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system for navigating and positioning an instrument in a body, wherein the instrument comprises a sensor for optical inspection of tissue in the body, the instrument being configured to generate a tissue signal, the system comprising:

a tissue-type determination device configured to receive the tissue signal from the instrument at times that correspond with a timestamp Ts, the tissue-type determination device being further configured to determine a set of parameters indicative of tissue type based on the tissue signal from the instrument;

a medical imaging device configured to form an image of an interior of the body, the medical imaging device being configured to record a temporal sequence of images, wherein each image is separated from a neighboring image in the temporal sequence by a temporal distance that corresponds with a timestamp Tf, wherein an interval between neighboring Tf timestamps is smaller than an interval between neighboring Ts timestamps;

an image processing unit time-synchronized with the tissue-type determination device, wherein the image processing unit is configured to establish a combined image of the interior of the body at each timestamp Tf that comprises (i) a current instrument position (xc, yc) and (ii) an indication of tissue-type at a previous spatial position of the instrument (xs, ys) that corresponds with a tissue signal retrieval location for a timestamp Ts so that the combined image of the interior of the body comprises both the current instrument position and the indication of tissue-type at the previous spatial position of the instrument that corresponds with the tissue signal retrieval location for the corresponding timestamp Ts; and a display unit for displaying the combined image of the interior of the body.

2. The system according to claim 1, wherein the sensor for optical inspection of tissue is configured for determining blood, water, fat, collagen, bile, beta-carotene content, oxygenation of blood and scattering parameters.

3. The system according to claim 1, wherein a color saturation level of the indication of tissue-type is indicative of a measured quantity of a tissue parameter.

4. The system according to claim 1, wherein the tissue-type determination device is connected to a spectrometer configured for transforming a signal from the tissue-type determination device into a spectrum.

5. The system according to claim 4, wherein the tissue parameter is determined based on the spectrum.

6. The system according to claim 1, wherein the tissue parameter is displayed as a solid line and a width of the solid line is an indicator of a tissue parameter determination inaccuracy.

7. The system according to claim 1, wherein the set of parameters indicative of tissue type based on the tissue signal from the instrument comprises:

performing multivariate statistical analysis, wherein the multivariate statistical analysis comprises one or more of (i) principal components analysis or (ii) partial least squares discriminant analysis.

8. A method comprising the steps of:
determining a sequence of images of an interior of a body at respective times that correspond with a timestamp Tf;
determining a sequence of sensor positions (xc, yc) of an instrument in the respective images of the interior of the body at the respective times that correspond with the timestamp Tf;
determining, at a time that corresponds with a timestamp Ts, a tissue parameter at a sensor position of the instrument, wherein the instrument comprises a sensor for optical inspection of tissue in the body, the instrument being configured to generate a tissue signal, wherein an interval between neighboring Tf timestamps is smaller than an interval between neighboring Ts timestamps;
determining, for each time that corresponds with a timestamp Ts, an indication of tissue-type at a spatial position (xs, ys) of the sensor for a corresponding timestamp Ts; and
displaying, via a display unit, an image that comprises a combination of (i) an image of the interior of the body at a corresponding timestamp Tf and (ii) a representation of tissue parameter at a previous sensor position at a time corresponding with a timestamp Ts.

9. The method according to claim 8, further comprising determining a color saturation level of the indication of tissue-type that is representative of a quantity of determined tissue parameter.

10. The method according to claim 8, wherein the tissue parameter is determined using an optical sensor, the method further comprising:
using a spectrum determined from a signal from the optical sensor for determining the tissue parameter.

11. The method according to claim 8, wherein the tissue parameter is displayed as a solid line and a width of the solid line is an indicator of a tissue parameter determination inaccuracy.

12. The method according to claim 8, wherein the determination of to the set of parameters indicative of tissue type comprises:
performing multivariate statistical analysis, wherein the multivariate statistical analysis comprises one or more of (i) principal components analysis or (ii) partial least squares discriminant analysis.

13. A computer program product comprising instructions which when executed on a digital processor, cause a computer to perform a method comprising the steps of determining a sequence of images of an interior of a body at respective times that correspond with a timestamp Tf,
determining a temporal sequence of sensor positions of an instrument in the respective images of the interior of the body at the respective times that correspond with the timestamp Tf,
determining, at a time that corresponds with a timestamp Ts, a tissue parameter at a sensor position of the instrument, wherein the instrument comprises a sensor for optical inspection of tissue in the body, the instrument being configured to generate a tissue signal, wherein an interval between neighboring Tf timestamps is smaller than an interval between neighboring Ts timestamps,
determining, for each time that corresponds with a timestamp Ts, an estimated sensor position based on a part of the temporal sequence of sensor positions for a time period around a time that corresponds with a corresponding timestamp Ts, and
displaying on a display unit an image that comprises a combination of an image of the interior of the body at a corresponding timestamp Tf and (ii) a representation of tissue parameter at a previous sensor position at a time corresponding with a timestamp Ts.

14. The computer program product according to claim 13, wherein the tissue parameter is displayed as a solid line and a width of the solid line is an indicator of a tissue parameter determination inaccuracy.

15. An instrument for use in a system for guiding the instrument in a body,
the instrument comprising an optical probe, and
the system for guiding the instrument comprising:
a tissue-type determination device configured to receiving a tissue signal from the instrument at times that correspond with a timestamp Ts, the tissue-type determination device configured to determine a set of parameters indicative of tissue type based on the tissue signal received from the instrument,
a medical imaging device configured for forming an image of an interior of the body, the medical imaging device recording a temporal sequence of images, wherein each image is separated from a neighboring image in the temporal sequence by a temporal distance that corresponds with a timestamp Tf, wherein an interval between neighboring Tf timestamps is smaller than an interval between neighboring Ts timestamps,
an image processing unit time-synchronized with the tissue-type determination device and the image processing unit, wherein the image processing unit is configured to establish a combined image of the interior of the body at each timestamp Tf that comprises (i) a current instrument position (xc, yc) and (ii) an indication of tissue-type at a previous spatial position of the instrument (xs, ys) that corresponds with a tissue signal retrieval location for a timestamp Ts so that the combined image of the interior of the body comprises both the current instrument position and the indication of tissue-type at the previous spatial position of the instrument that corresponds with the tissue signal retrieval location for the corresponding timestamp Ts, and
a display unit for displaying the combined image of the interior of the body.

\* \* \* \* \*